(12) United States Patent
Wagle et al.

(10) Patent No.: US 6,380,192 B1
(45) Date of Patent: *Apr. 30, 2002

(54) TRIAZINE COMPOUNDS AND METHOD OF USE THEREFOR

(75) Inventors: Dilip R. Wagle, Valley Cottage, NY (US); Michael E. Lankin, Cedar Grove, NJ (US); San-Bao Hwang, Sudbury, MA (US)

(73) Assignee: Alteon, Inc., Ramsey, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/552,949

(22) Filed: Apr. 20, 2000

Related U.S. Application Data

(60) Provisional application No. 09/233,551, filed on Jan. 20, 1999, now Pat. No. 6,060,470, provisional application No. 08/825,114, filed on Mar. 27, 1997, now Pat. No. 5,932,578, provisional application No. 60/014,387, filed on May 28, 1996, and provisional application No. 60/016,822, filed on May 3, 1996.

(51) Int. Cl.$^7$ .................. C07D 253/07; A61K 31/53

(52) U.S. Cl. ........................... 514/242; 544/182

(58) Field of Search ........................... 514/242; 544/182

(56) References Cited

U.S. PATENT DOCUMENTS

| | | |
|---|---|---|
| 3,961,936 A | 6/1976 | Westphal et al. ............... 71/93 |
| 4,036,632 A | 7/1977 | Westphal et al. ............... 71/93 |
| 4,057,417 A | 11/1977 | Dickore et al. ............... 713/93 |
| 4,386,953 A | 6/1983 | Kranz et al. ............... 71/93 |
| 4,470,842 A | 9/1984 | Kranz et al. ............... 71/93 |
| 4,547,216 A | 10/1985 | Bohner ............... 71/93 |
| 4,632,694 A | 12/1986 | Tocker ............... 71/93 |
| 4,758,583 A | 7/1988 | Cerami et al. ............... 514/399 |
| 5,076,833 A | 12/1991 | Krantz et al. ............... 71/93 |
| 5,935,578 A | 8/1999 | Wagle ............... 514/242 |

FOREIGN PATENT DOCUMENTS

| | | |
|---|---|---|
| EP | 0150677 | 8/1985 |
| WO | WO 92/11853 | 7/1992 |
| WO | WO 94/11490 | 5/1994 |

OTHER PUBLICATIONS

J. Chem. Soc. Perkin Trans. 1 (1986) 2037–2049 (Molina, et al.), Iminophosphorane–mediated Synthesis of [1,2,4] Triazolo . . .

Chemical Abstract. 78: vol. 125, No. 14 (1996) 184106t. Synthesis, structure, and cytotoxicity evaluation . . .

Brownlee, "The Pathological Implications of Protein Glycation," Clin. Invest. Med., vol. 18, No. 4, pp. 275–281, 1995.

Brownlee, "Advanced Protein Glycosylation in Diabetes and Aging," Annu. Rev. Med., vol. 46, pp. 223–224, 1995.

Vlassara et al., "Biology of Disease," Laboratory Investigation, vol. 70, No. 2, pp. 138–151, 1994.

Eia et al., "Synthesis and Condensation reactions of Some 6–Substitutedbenzyl–3–Hydrazino–2,5–Dihydro–1,2, 4–Triazin–5–Ones," Egypt. J. Pharm. Sci., vol. 31, No. 1–4, pp. 337–342, 1990.

Striker et al., "Administration of AGEs in vivo Induces Extracellular Matrix Gene Expression," Nephrol. Dial. Transplant, vol. 11, Suppl. 5, MEDLINE abstract provided, pp. 62–65, 1996.

Daunis et al., "Effect of the substituent at position 6 of 3–hydrozino–5–hydraxytriazines on the Cyclization into S–triazolo–as–triazine", Bull. Soc. Chim., vol. 3–4 Part 2, pp. 857–863, 1975.

Molina et al., "Iminophosphorane–mediated Synthese of > 1,2,4!Triazolo> 5,1–c!>1,2,4!Triazines," J. Chem. Soc. Perkin Trans. I, vol. 12, pp. 2037–2049, 1986.

Basnak et al. (1975) Collect. Czech. Commun. 40:1038–42.

Bierowska–Charytonowicz et al. (1976) Arch. Immun. Ther. Exp. 24:883–99.

Bierowska–Charytonowicz et al. (1973) Rocz. Chem. 47(11):2199–201.

Brownlee et al., Science, 232, 99. 1629–1632 (1986).

Brownlee et al., Diabetes, 35, Suppl. 1, p. 42A (1986).

Essassi et al. (1977) Tetrahedron 33 (21):2807–12.

Lachowicz et al. (1974) Act. Microbiol. Pol., Ser. A. 6(2):147–54.

Lavergne et al. (1975) J. Heterocyclic Chem. 12(6):1095–101.

Molina et al. (1989) Heterocylces 29(8):1607–13.

Ueda et al. (1964) Chem. Pharm. Bul. 12:100–3.

*Primary Examiner*—Richard L. Raymond
*Assistant Examiner*—Kahsay Habte
(74) *Attorney, Agent, or Firm*—Dechert

(57) ABSTRACT

The present invention relates to compositions and methods for inhibiting nonenzymatic cross-linking (protein aging). Accordingly, a composition is disclosed which comprises a substituted 1,2,4-triazine of the formula (I)

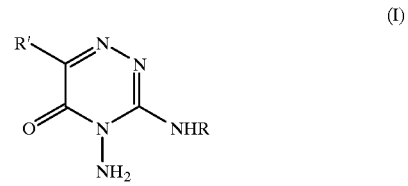

and the biologically and pharmaceutically acceptable salts thereof; capable of inhibiting the formation of advanced glycosylation endproducts of target proteins. The method comprises contacting the target protein with the composition. Both industrial and therapeutic applications for the invention are envisioned, as food spoilage and animal protein aging can be treated.

15 Claims, No Drawings

TRIAZINE COMPOUNDS AND METHOD OF USE THEREFOR

This application is a continuation of Ser. No. 09/233,551, filed Jan. 20, 1999, now U.S. Pat. No. 6,060,470, which is a continuation of Ser. No. 08/825,114 filed Mar. 27, 1997, now U.S. Pat. No. 5,932,578, which claims priority of Ser. No. 60/014,387 filed May 28, 1996 and Ser. No. 60/016,822 filed May 3, 1996.

BACKGROUND OF THE INVENTION

The present invention relates generally to the aging of proteins resulting from their reaction with glucose and other reducing sugars, and more particularly to the inhibition of the reaction of nonenzymatically glycosylated proteins and the often resultant formation of advanced glycosylation (glycation) endproducts and cross-links.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Further studies have suggested that stored and heat treated foods undergo nonenzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin A1c. The reaction has also been found to occur with a variety of other body proteins, such as lens crystallins, collagen and nerve proteins. See Bucala et al., "Advanced Glycosylation; Chemistry, Biology, and Implications for Diabetes and Aging" in *Advances in Pharmacology*, Vol. 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In U.S. Pat. No. 4,758,583, a method and associated agents were disclosed that served to inhibit the formation of advanced glycosylation endproducts by reacting with an early glycosylation product that results from the original reaction between the target protein and glucose. Accordingly, inhibition was postulated to take place as the reaction between the inhibitor and the early glycosylation product appeared to interrupt the subsequent reaction of the glycosylated protein with additional protein material to form the cross-linked late-stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility.

SUMMARY OF THE INVENTION

In accordance with the present invention, a method and compositions are disclosed for the inhibition of the advanced glycosylation of proteins (protein aging). In particular, the compositions comprise agents for inhibiting nonenzymatic cross-linking (protein aging) due to the formation of advanced glycosylation (glycation) endproducts. The agents may be selected from those materials capable of reacting with an early glycosylation product from the reaction of glucose with proteins and preventing further reactions. Cross-linking caused by other reactive sugars present in vivo or in foodstuffs, including ribose, galactose and fructose would also be prevented by the methods and compositions of the present invention.

The agents comprise substituted triazine compounds having the following structural formula:

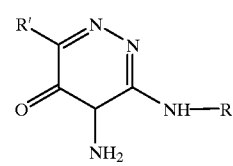

(I)

wherein R is hydrogen or an amino group;

R' is a cycloalkyl group;
an aralkyl group wherein the alkyl portion contains from 1 to 6 carbon atoms, and the aryl portion is optionally substituted by one to three hydroxy, lower alkoxy or nitro groups;
a heteroaryl group containing from 1 to 3 heteroatoms selected from the group consisting of sulfur, oxygen and nitrogen;
a group of the formula

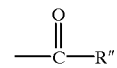

wherein R" is hydroxy, a lower alkoxy group, an aryl group optionally substituted by a lower alkoxy group, or a group of the formula

—NR'''NH$_2$ wherein R''' is hydrogen or a methyl group; or
a lower alkyl or alkylene group, optionally substituted by hydroxy or a group of the formula

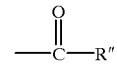

wherein R" is hydroxy, a lower alkoxy group, an aryl group optionally substituted by a lower alkoxy group, or a group of the formula

—NR'''NH$_2$ wherein R''' is hydrogen or a methyl group;
and their biologically or pharmaceutically acceptable acid addition salts; and mixtures thereof, and a carrier therefor.

The compounds, and their compositions, utilized in this invention appear to react with an early glycosylation product thereby preventing the same from later forming the advanced glycosylation end products which lead to protein cross-links, and thereby, to protein aging.

The present invention also relates to a method for inhibiting protein aging by contacting the initially glycosylated protein at the stage of the early glycosylation product with a quantity of one or more of the agents of the present invention, or a composition containing the same. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

The ability to inhibit the formation of advanced glycosylation endproducts carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts carries the promise of treatment for diabetes and, of course, improving the quality and, perhaps, duration of animal life.

The present agents are also useful in the area of personal appearance and hygiene, as they prevent the staining of teeth by cationic anti-microbial agents with anti-plaque properties, such as chlorhexidine.

Accordingly, it is a principal object of the present invention to provide a method for inhibiting the extensive cross-linking of proteins that occurs as an ultimate consequence of the reaction of the proteins with glucose and other reactive sugars, by correspondingly inhibiting the formation of advanced glycosylation endproducts.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a still further object of the present invention to provide therapeutic methods of treating the adverse consequences of protein aging by resort to the aforesaid method and agents.

It is a still further object of the present invention to provide a method of inhibiting the discoloration of teeth by resort to the aforesaid method and agents.

It is a still further object of the present invention to provide compositions including pharmaceutical compositions, all incorporating the agents of the present invention.

It is still further object of the present invention to provide novel compounds, as well as processes for their preparation, for use in the methods and compositions of the present invention.

Other objects and advantages will become apparent to those skilled in the art from a consideration of the ensuing description.

DETAILED DESCRIPTION OF THE PREFERRED EMBODIMENT

In accordance with the present invention, agents, compositions including pharmaceutical compositions containing said agents and associated methods have been developed which are believed to inhibit the formation of advanced glycosylation endproducts in a number of target proteins existing in both animals and plant material.

In particular, the invention relates to a composition which may contain one or more agents comprising substituted triazine compounds having the structural formula:

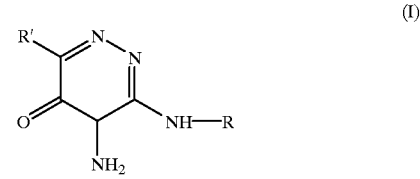

(I)

wherein R is hydrogen or an amino group;
R' is a cycloalkyl group;
an aralkyl group wherein the alkyl portion contains from 1 to 6 carbon atoms, and the aryl portion is optionally substituted by one to three hydroxy, lower alkoxy or nitro groups;
a heteroaryl group containing from 1 to 3 heteroatoms selected from the group consisting of sulfur, oxygen and nitrogen;
a group of the formula

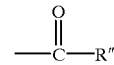

wherein R" is hydroxy, a lower alkoxy group, an aryl group optionally substituted by a lower alkoxy group, or a group of the formula

—NR'''NH$_2$ wherein R''' is hydrogen or a methyl group; or
a lower alkyl or alkylene group, optionally substituted by hydroxy or a group of the formula

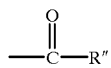

wherein R'' is hydroxy, a lower alkoxy group, an aryl group optionally substituted by a lower alkoxy group, or a group of the formula

wherein R''' is hydrogen or a methyl group;
and their biologically or pharmaceutically acceptable acid addition salts; and mixtures thereof, and a carrier therefor.

The lower alkyl groups referred to above preferably contain 1–6 carbon atoms and include methyl, ethyl, propyl, butyl, pentyl, hexyl, and the corresponding branched-chain isomers thereof. The lower alkylene groups likewise contain from 2 to 6 carbon atoms, and are exemplified by ethylene, propylene, butylene, pentylene, hexylene, and the corresponding branched chain isomers thereof. These groups are optionally substituted by one or more hydroxy groups, or a group of the formula

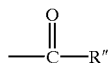

wherein R'' is hydroxy, a lower alkoxy group, an aryl group optionally substituted by a lower alkoxy group, or a group of the formula

wherein R''' is hydrogen or a methyl group.

These substituted carbonyl compounds are thus carboxy, alkoxycarbonyl, arylcarbonyl or hydrazinylcarbonyl compounds wherein the alkyl portion contains from 1 to 6 carbon atoms as described hereinabove. Similarly, the aryl portion is as defined hereinbelow.

The aryl groups encompassed by the above formula are those containing 6–10 carbon atoms, such as naphthyl, phenyl and lower alkyl substituted-phenyl, e.g., tolyl and xylyl, and are optionally substituted by 1–3 hydroxy, lower alkoxy or nitro groups. Preferred aryl groups are phenyl and methoxyphenyl groups.

Where the possibility exists for substitution of a phenyl or aryl ring, the position of the substituents may be ortho, meta, or para to the point of attachment of the phenyl or aryl ring to the nitrogen of the hydrazine group.

The cycloalkyl groups contain from 1 to 7 carbon atoms, and are typified by cyclopropyl, cyclobutyl, cyclopentyl, cyclohexyl, and cycloheptyl, optionally substituted by one or more lower alkyl groups.

The heteroaryl groups of the compounds of formula I typically contain from 5 to 6 ring atoms, of which 1 to 3 are selected from the group consisting of oxygen, nitrogen and sulfur. Representative of such groups are 2-pyridyl, 3-pyridyl, 4-pyridyl, 2-thienyl, 3-thienyl, 2-furanyl, 3-furanyl, 2-pyrrolyl, and 3-pyrrolyl, optionally substituted by one or more lower alkyl groups.

The lower alkoxy groups contain 1–6, and preferably 1–3, carbon atoms and are illustrated by methoxy, ethoxy, n-propoxy, isopropoxy and the like.

For the purposes of this invention equivalent to the compounds of formula (I) are the biologically and pharma-ceutically acceptable acid addition salts thereof. Such acid addition salts may be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by Formula I, certain substituents are preferred. For instance, the compounds wherein R is a lower alkyl group, and particularly those wherein R is a methyl group, are preferred.

Representative compounds of the present invention are:
3,4-diamino-6-methyl-1,2,4-triazine-5(4H)-one;
3,4-diamino-6-(4-hydroxybenzyl)-1,2,4-triazine-5(4H)-one;
3,4-diamino-6-ethyl-1,2,4-triazine-5(4H)-one;
3,4-diamino-6-benzyl-1,2,4-triazine-5(4H)-one;
3,4-diamino-6-(2-thienyl)-1,2,4-triazine-5(4H)-one;
3,4-diamino-6-(3,4-dimethoxystyryl)-1,2,4-triazine-5(4H)-one;
3,4-diamino-6-(2'-nitrobenzyl)-1,2,4-triazine-5(4H)-one;
3,4-diamino-6-(2'-carboxyethyl)-1,2,4-triazine-5(4H)-one;
3,4-diamino-6-isopropyl-1,2,4-triazine-5(4H)-one;
3,4-diamino-6-(2-methypropyl)-1,2,4-triazine-5(4H)-one;
3,4-diamino-6-propyl-1,2,4-triazine-5(4H)-one;
3,4-diamino-6-butyl-1,2,4-triazine-5(4H)-one;
3,4-diamino-6-(1-methylpropyl)-1,2,4-triazine-5(4H)-one;
3,4-diamino-6-cyclopropyl-1,2,4-triazine-5(4H)-one;
3,4-diamino-6-phenethyl-1,2,4-triazine-5(4H)-one;
3,4-diamino-6-carboxyethyl-1,2,4-triazine-5(4H)-one;
3,4-diamino-6-(2'-ethoxycarbonylethyl)-1,2,4-triazine-5(4H)-one;
3,4-diamino-6-(1'-ethoxycarbonylethyl)-1,2,4-triazine-5(4H)-one;
3,4-diamino-6-(1'-ethoxycarbonylheptyl)-1,2,4-triazine-5(4H)-one;
3,4-diamino-6-(3'-methoxyphenylcarbonylmethylene)-1,2,4-triazine-5(4H)-one;
6-(3,4-diamino-5(4H)-one-1,2,4-triazinyl)hydrazide;
3-[6'-(3',4'-diamino-5'(4H)-one-1',2',4'-triazinyl)]-propionic hydrazide;
2-methyl-6'-(3',4'-diamino-5(4H)-one-1,2,4-triazinyl) hydrazide;
3,4-diamino-6-(1',1'-dimethyl-2'-hydroxyethyl)-1,2,4-triazine-5(4H)-one;
4-amino-3-hydrazino-6-methyl-1,2,4-triazine-5(4H)-one;
4-amino-3-hydrazino-6-(4-hydroxybenzyl)-1,2,4-triazine-5(4H)-one;
4-amino-3-hydrazino-1,2,4-triazine-5(4H)-one; and their biologically and pharmaceutically acceptable salts.

The above compounds are capable of inhibiting the formation of advanced glycosylation endproducts on target proteins. The cross-linking of the protein to form the advanced glycosylation endproduct contributes to the entrapment of other proteins and results in the development in vivo of conditions such as reduced elasticity and wrinkling of the skin, certain kidney diseases, atherosclerosis, osteoarthritis and the like. Similarly, plant material that undergoes nonenzymatic browning deteriorates and, in the case of foodstuffs, become spoiled or toughened and, consequently, inedible. Thus, the compounds employed in accordance with this invention inhibit this late-stage Maillard effect and intervene in the deleterious changes described above.

The rationale of the present invention is to use agents which block the post-glycosylation step, i.e., the formation of fluorescent chromophores, the presence of which chromophores is associated with, and leads to adverse sequelae of diabetes and aging. An ideal agent would prevent the formation of the chromophore and its associate cross-links of proteins to proteins and trapping of proteins on the other proteins, such as occurs in arteries and in the kidney.

The chemical nature of the early glycosylation products with which the compounds of the present invention are believed to react may vary, and accordingly the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformylglycosylpyrroles.

The compositions useful in the present invention comprise or contain agents capable of reacting with the active carbonyl intermediate of an early glycosylation product. Suitable agents are the compounds of Formula I of the present invention. The present invention likewise relates to methods for inhibiting the formation of advanced glycosylation endproducts, which comprise contacting the target proteins with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has, as indicated earlier, been identified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein cross-linking through advanced glycosylation product formation can decrease solubility of structural proteins such as collagen in vessel walls and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. For these reasons, the progressive occlusion of diabetic vessels induced by chronic hyperglycemia has been hypothesized to result from excessive formation of glucose-derived cross-links. Such diabetic microvascular changes and microvascular occlusion can be effectively prevented by chemical inhibition of advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., *Lab. Invest.*, 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., *Science*, 232, pp. 1629–1632 (1986) to this additional target organ of complication of diabetes. Also, an additional study showed the reduction of immunoglobulin trapping in the kidney by aminoguanidine (Brownlee et al., *Diabetes* 35, Suppl. 1, p. 42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition of the formation of advanced glycosylation endproducts (AGEs), by the teaching of the present invention, may prevent late, as well as early, structural lesions due to diabetes, as well as changes during aging caused by the formation of AGEs.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits.

A further consequence of diabetes is the hyperglycemia-induced matrix bone differentiation resulting in decreased bone formation usually associated with chronic diabetes. In animal models, diabetes reduces matrix-induced bone differentiation by 70%.

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, by subcutaneous, intravenous or intraperitoneal injection, as well as by other conventional means. Administration of the agents may take place over an extended period of time at a dosage level of, for example, up to about 30 mg/kg.

As noted earlier, the invention also extends to a method of inhibiting the discoloration of teeth resulting from nonenzymatic browning in the oral cavity which comprises administration to a subject in need of such therapy an amount effective to inhibit the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, *J. Dent. Res.*, 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit the formation of advanced glycosylation endproducts. This amount will, of course, vary with the particular agent being utilized and the particular dosage form, but typically is in the range of 0.01% to 1.0%, by weight, of the particular formulation.

Certain of the compounds encompassed by Formula I are novel compounds which can be prepared by modifications of chemical syntheses well-known in the art. These compounds are those compounds of formula I wherein the R group is an amino group, with the proviso that when R' is a lower alkyl group, it is substituted as defined in formula I hereinabove and the compounds of formula I wherein the R group is hydrogen, with the proviso that when R' is a lower alkyl group, it is substituted by hydroxy or a group of the formula

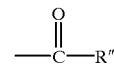

wherein R" is hydroxy, a lower alkoxy group, an aryl group optionally substituted by a lower alkoxy group, or a group of the formula

wherein R'" is hydrogen or a methyl group. These compounds can be represented by the structural formula (Ia):

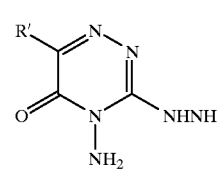

(Ia)

wherein when R is an amino group, then
R' is a cycloalkyl group;
an aralkyl group wherein the alkyl portion contains from 1 to 6 carbon atoms, and the aryl portion is optionally substituted by one to three hydroxy, lower alkoxy or nitro groups;
a heteroaryl group containing from 1 to 3 heteroatoms selected from the group consisting of sulfur, oxygen and nitrogen;

a group of the formula

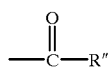

wherein R" is hydroxy, a lower alkoxy group, an aryl group optionally substituted by a lower alkoxy group, or a group of the formula

—NR'''NH$_2$ wherein R'" is hydrogen or a methyl group; or
a lower alkyl or alkylene group, optionally substituted by hydroxy or a group of the formula

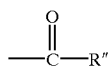

wherein R" is hydroxy, a lower alkoxy group, an aryl group optionally substituted by a lower alkoxy group, or a group of the formula

—NR'''NH$_2$ wherein R'" is hydrogen or a methyl group;
or when R is hydrogen; then
R' is a cycloalkyl group;
a group of the formula

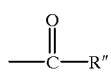

wherein R" is hydroxy, a lower alkoxy group, an aryl group optionally substituted by a lower alkoxy group, or a group of the formula

—NR'''NH$_2$ wherein R'" is hydrogen or a methyl group; or a lower alkyl group or an alkylene-group, optionally substituted by hydroxy or a group of the formula

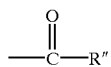

wherein R" is hydroxy, a lower alkoxy group, an aryl group optionally substituted by a lower alkoxy group, or a group of the formula

—NR'''NH$_2$ wherein R'" is hydrogen or a methyl group;
with the proviso that when R' is a lower alkyl group, then it must be a substituted;
and their biologically or pharmaceutically acceptable acid addition salts.

The following compounds of the present invention are thus novel and heretofore unknown in the prior art:

3,4-diamino-6-(3,4-dimethoxystyryl)-1,2,4-triazine-5 (4H)-one hydrochloride;
3,4-diamino-6-(2'-carboxyethyl)-1,2,4-triazine-5(4H)-one hydrochloride;
3,4-diamino-6-cyclopropyl-1,2,4-triazine-5(4H)-one hydrochloride;
3,4-diamino-6-carboxyethyl-1,2,4-triazine-5(4H)-one hydrochloride;
3,4-diamino-6-(2'-ethoxycarbonylethyl)-1,2,4-triazine-5(4H)-one hydrochloride;
3,4-diamino-6-(2'-ethoxycarbonylethyl)-1,2,4-triazine-5(4H)-one hydrochloride;
3,4-diamino-6-(1'-ethoxycarbonylheptyl)-1,2,4-triazine-5(4H)-one hydrochloride;
3,4-diamino-6-(3'-methoxyphenylcarbonylmethylene)-1,2,4-triazine-5(4H)-one;
6-(3,4-diamino-5(4H)-one-1,2,4-triazinyl)hydrazide;
6-(3,4-diamino-5(4H)-one-1,2,4-triazinyl)hydrazide hydrochloride;
3-[6'-(3',4'-diamino-5'(4H)-one-1',2',4'-triazinyl)]-propionic hydrazide;
2-methyl-6'-(3',4'-diamino-5(4H)-one-1,2,4-triazinyl) hydrazide;
3,4-diamino-6-(1',1'-dimethyl-2'-hydroxyethyl)-1,2,4-triazine-5(4H)-one hydrochloride; and
4-amino-3-hydrazino-6-(4-hydroxybenzyl)-1,2,4-triazine-5(4H)-one.

The compounds of formula I can be prepared according to the methods described in Dornow et al., *Chem. Ber.* 97:2647 and 2173 (1964), Veda et al., *Chem. Pharm. Bul.* (1964), 12, 100, *J. Chem Soc., Perkin Trans.*, 1(12), 2037–2049 (1986). or those of U.S. Pat. Nos. 4,036,632 and 3,961,936, or as shown in the various schemes below. These references, in particular, describe the preparation of the compounds of formula I wherein R is hydrogen.

The triazines of formula I wherein R' is other than a lower alkyl group substituted by a C(O)R wherein R" is a hydrazine or methylhydrazine group can be prepared by the synthetic route shown below in Scheme I.

In the synthetic route shown as Scheme I, the appropriate pyruvic acid derivative of formula II wherein R'* is a cycloalkyl group; an aralkyl group wherein the alkyl portion contains from 1 to 6 carbon atoms, and the aryl portion is optionally substituted by 1 to three hydroxy, lower alkoxy or nitro groups; a heteroaryl group containing from 1 to 3 heteroatoms selected from the group consisting of sulfur, oxygen and nitrogen; a group of the formula

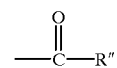

wherein R" is hydroxy, a lower alkoxy group, an aryl group optionally substituted by a lower alkoxy group; a lower alkyl group, optionally substituted by hydroxy or a group of the formula

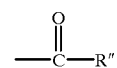

wherein R" is hydroxy, a lower alkoxy group, an aryl group optionally substituted by a lower alkoxy group, and X is a hydroxy, ethoxy or sodium salt of the hydroxide, is reacted with a 1,3-diaminoguanidine acid addition salt to afford the desired compound of formula I wherein R' is other than a lower alkyl group substituted by a C(O)R" wherein R" is a hydrazine or methylhydrazine group. This reaction is typically conducted in an alkanol or aqueous alkanol solvent, at the reflux temperature of the solvent system. Typical reaction times vary according to the precise nature of the particular reactants, but are usually in the range of 12–36 hours.

Scheme I

Synthesis of 3,4-diamino-6-substituted-1,2,4-triazin-5(4H)-ones

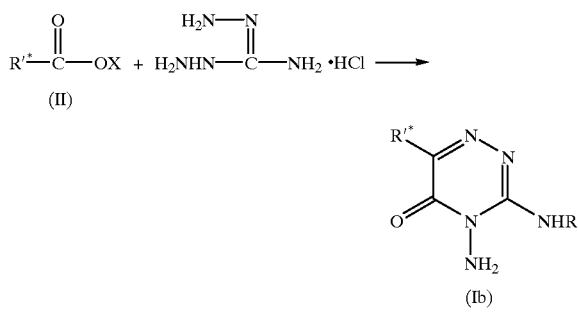

The compounds of formula I wherein R' is a lower alkyl group substituted by a C(O)R" wherein R" is a hydrazine or methylhydrazine group can be prepared by the synthetic route shown below in Scheme II.

In this synthetic route, a compound of formula I wherein R' is an alkoxycarbonyl group is utilized as the starting material to prepare the corresponding compound of formula I wherein R' is a lower alkyl group substituted by a C(O)R" wherein R" is a hydrazine or methylhydrazine group. Typically, the compound of formula I wherein R' is an alkoxycarbonyl group is treated with anhydrous hydrazine or methylhydrazine and water at reflux temperatures. Typical times vary from about 0.5 to 3 hours. Preferably, the resultant product, which is the free base, is converted to the acid addition salt, preferably one such as the hydrochloride, without isolation. The salt form is then crystallized to give the desired product.

Scheme II

Synthesis of 6-(3',4'-Diamino-5(4H)-one-1,2,4-triazinyl)-hydrazide)

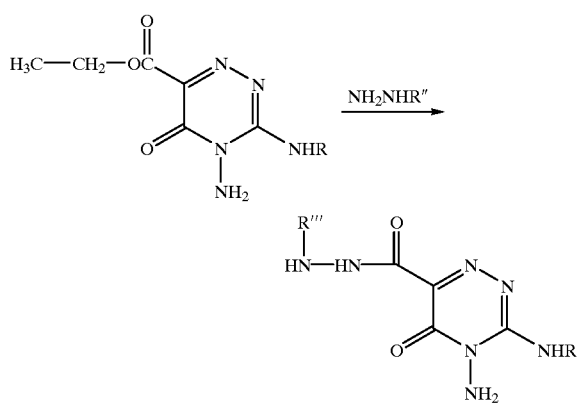

The compounds of formula I wherein R' is a lower alkyl group substituted by a hydroxy group can also be prepared by the synthetic route shown in Scheme III. In this scheme, a dihydro4,4-dimethyl-2,3-furandione is utilized in place of the compound of formula II of Scheme I. Other reaction conditions are generally similar. Thus afforded are the particular hydroxyalkyl compounds wherein the lower alkyl group is an ethyl or propyl group, optionally substituted by one or more lower alkyl groups.

Scheme III

Synthesis of 3,4-Diamino-6-(1',1'-dimethyl-2'-hydroxyethyl)-1,2,4-triazin-5(4H)-one hydrochloride

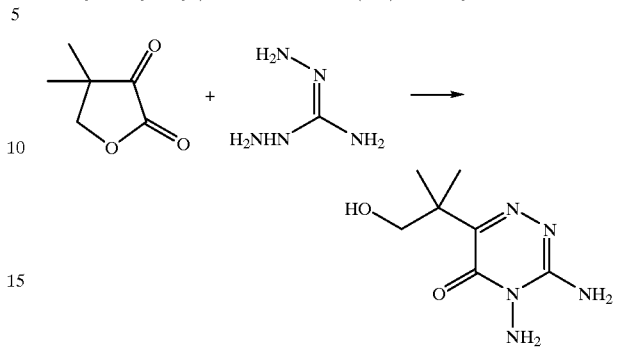

The following examples are illustrative of the invention.

EXAMPLE 1

General Procedure for the Synthesis of 3,4-diamino-6-substituted-1,2,4-triazin-5(4H)-ones A mixture of 1,3-diaminoguanidine monohydrochloride (10 mmole) and the appropriate pyruvic acid derivative of formula II (10 mmole) were refluxed in ethanol (25 ml). Water was added dropwise until the reaction mixture formed a clear solution. This solution was then refluxed overnight, and then cooled to room temperature. The desired product, which separated upon standing, was filtered, dried and crystallized from an ethanol/water mixture. In the case where no product separated, the mixture was evaporated to dryness and the residue was crystallized from ethanol/water mixture.

When the sodium salt of the pyruvic acid derivative of formula II was used as a starting material, the resultant product was usually in the form of the free base. This free base form could then be converted into the corresponding hydrochloride salt by treatment of the free base with 2N hydrochloric acid.

The reaction was typically carried out using ethanol as the solvent system when the derivative of pyruvic acid of formula II was an ester (X=ethoxy) was used.

Using the following pyruvic acid derivatives of formula II as starting materials, the compounds of formula I, described in Table 1, were prepared:

(1) pyruvic Acid
(2) 4-hydroxyphenylpyruvic acid
(3) 2-ketobutyric acid
(4) phenylpyruvic acid
(5) 2-thiopheneglyoxylic acid
(6) 2-(3,4-dimethoxystyryl)glyoxylic acid
(7) 2-nitrophenyl pyruvic acid
(8) 2-ketoglutaric acid
(9) 2-methyl-2-oxobutanoic acid, sodium salt
(10) 4-methyl-2-oxobutanoic acid, sodium salt
(11) 2-oxopentanoic acid, sodium salt
(12) 2-oxohexanoic acid, sodium salt
(13) (±)-3-methyl-2-oxopentanoic acid, sodium salt
(14) cyclopropylglyoxylic acid

(15) ethyl 2-oxo-4-phenylbutyrate
(16) diethyl ketomalonate
(17) diethyl 2-oxoglutarate
(18) diethyl oxalpropionate
(19) diethyl 3-heptyl-2-oxosuccinate
(20) ethyl 3-(3-methoxybenzoyl) pyruvate
(21) glyoxylic acid The physical data of the corresponding triazines (1–21) is given in Table 1 below. (X indicates the number of moles of the hydrochloride salt in the product)

TABLE 1

Physical Data of Triazine Compounds

| NO. | R' | $R^2$ | X | M.P. ° | Yield % |
|---|---|---|---|---|---|
| 1 | $H_3C-$ | H | 0 | 260 | 90 |
| 2 | HO-C$_6$H$_4$-CH$_2-$ (4-hydroxybenzyl) | H | 1 | 278–279 (dec) | 80 |
| 3 | $H_3C-CH_2-$ | H | 1 | 239–240 (dec) | 48 |
| 4 | C$_6$H$_5$-CH$_2-$ (benzyl) | H | 1 | 218–222 (dec) | 33 |
| 5 | 2-thienyl | H | 1 | 265–266 (dec) | 21 |
| 6 | 3,4-dimethoxyphenyl-CH=CH- | H | 1 | 245–246 | 16 |
| 7 | 2-nitrobenzyl | H | 1 | 239–241 (dec) | 43 |
| 8 | $HOOC-CH_2-CH_2-$ | H | 0 | 247–248 (dec) | 45 |
| 9 | $(CH_3)_2-CH_2-$ | H | 1 | 166–168 | 22 |
| 10 | $(CH_3)_2-CH-CH_2-$ | H | 0 | 190–192 | 48 |
| 11 | $(CH_3)_2-CH-CH_2$ | H | 1 | 260–262 (dec) | 59 |
| 12 | $H_3C-CH_2-CH_2-$ | H | 1 | 73 |  |
| 13 | $H_3C-(CH_2)_3-$ | H | 1 | 166–167 | 36 |
| 14 | $H_3C-CH_2-CH(CH_3)-$ | H | 0 | 189–191 | 65 |
| 15 | cyclopropyl | H | 0 | 213–214 (dec) | 17 |
| 16 | C$_6$H$_5$-CH$_2$-CH$_2-$ | H | 1 | 225–226 | 62 |
| 17 | $H_3C-CH_2-C(=O)-O-$ | H | 1 | 227–229 (dec) | 64 |
| 18 | $H_3C-CH_2O-C(=O)-CH_2-CH_2-$ | H | 1 | 205–207 | 53 |

TABLE 1-continued

Physical Data of Triazine Compounds

| NO. | R' | R² | X | M.P. ° | Yield % |
|---|---|---|---|---|---|
| 19 | 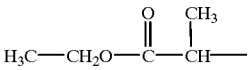 | H | 1 | 185–186 | 39 |
| 20 | 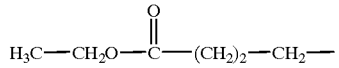 | H | 1 | 185–186 | 31 |
| 21 | 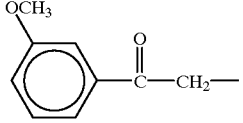 | H | 1 | 185–187 | 52 |

EXAMPLE 2

Synthesis of 6-(3',4'-diamino-5-one-1,2,4-triazinyl)-hydrazide 3,4-Diamino-6-carboxyethyl-1,2,4-triazin-5(4H)-one hydrochloride (1.59, 6.36 mmole) was taken in methanol (15 ml). Anhydrous hydrazine (156.25 mmole) and water 1 ml) was added and refluxed for 1 hour. On cooling to room temperature, the product which separated was filtered, dried and crystallized from ethanol to give 6-(3',4'-diamino-5 (4H)-one-1,2,4-triazinyl)hydrazide, in a yield of 60%, to give a product having a m.p. of >340° C.

This compound was converted into its dihydrochloride by treatment with 2N hydrochloric acid. The product, 6-(3',4'-diamino-5(4H)-one-1,2,4 -triazinyl)hydrazide dihydrochloride, was crystallized from ethanol/water mixture in 77% yield, and exhibits a m.p. of 134–135° C. (dec).

Using same procedure with methyhydrazine as a starting material, 2-methyl-[6'-(3',4'-diamino-5(4H)-one-1,2,4-triazinyl)]hydrazide, m.p. 126–128°, and 2-methyl-[6'-(3',4'-diamino-5(4H)-one-1,2,4-triazinyl)]hydrazide dihydrochloride, m.p. 178–180° (dec) were prepared.

EXAMPLE 3

Synthesis of 3,4-diamino-6-(1',1'-dimethyl-2'-hydroxyethyl-1,2,4-triazin-5(4H)-one hydrochloride Dihydro-4,4-dimethyl-2,3-furandione (2 g, 15.6 mmole) and 1,3-diaminoguanidine monohydrochloride (12.96 g, 15.61 mmole) were dissolved in ethanol and the resulting solution heated to reflux temperatures. To the refluxing reaction mixture, was added water until a clear solution was obtained. The mixture was then refluxed overnight, cooled to room temperature and stored at –20° C. overnight. The product which separated was filtered and dried. It was crystallized from a mixture of ethanol and water to give 3,4-diamino-6-(1',1'-dimethyl-2'-hydroxyethyl)-1,2,4-triazin-5(4H)-one hydrochloride (2.24 g, 61%), m.p. 221–222° C. (dec).

EXAMPLE 4

Synthesis of 4-amino-3-hydrazino-6-(4'-hydroxybenzyl)-1,2,4-triazin-5(4H)-one hydrochloride 4-Hydroxyphenylpyruvic acid (2 g, 11 mmole) and tri-aminoguanidine monohydrochloride (2.21 g, 15.78 mmole) were taken up in ethanol (25 ml) and heated until reflux. A few drops of water was added until the reaction mixture was clear. The resultant mixture was refluxed 24 hours and cooled to room temperature. The solid which separated was filtered, dried and crystallized from ethanol/water to give the title product (2 g, 47%), m.p. 209–210° C. (dec).

In a similar manner, 4-amino-3-hydrazino-6-methyl-1,2, 4-triazin-5(4H)-one hydrochloride, m.p. 195–196° C. and 4-amino-3-hydrazino-1,2,4-triazin-5(4H)-one hydrochloride, m.p. 260–261° C., were prepared.

EXAMPLE 5

The following method was used to evaluate the ability of the compounds of the present invention to inhibit the cross-linking of glycated bovine serum albumin (AGE-BSA) to the rat tail tendon collagen coated 96-well plate.

The AGE-BSA was prepared by incubating BSA at a concentration of 200 mg per ml with 200 mM glucose in 0.4 M sodium phosphate buffer, pH 7.4 at 37° C. for 12 weeks. The glycated BSA was then extensively dialyzed against phosphate buffer solution (PBS) for 48 hours with additional 5 times buffer exchanges. The rat tail tendon collagen coated plate was blocked first with 300 μl of superbloc blocking buffer (Pierce #37515X) for one hour. The blocking solution was removed from the wells by washing the plate twice with PBS-Tween 20 solution (0.05% Tween 20) using a NUNC-multiprobe or Dynatech ELISA-plate washer. Cross-linking of AGE-BSA (1 to 10 μg per well depending on the batch of AGE-BSA) to rat tail tendon collagen coated plate was performed with and without the testing compound dissolved in PBS buffer at pH 7.4 at the desired concentrations by the addition of 50 μl each of the AGE-BSA diluted in PBS or in the testing compound at 37° C. for 4 hours. The unbrowned BSA in PBS buffer with or without testing compound were added to the separate wells as the blanks. The un-cross-linked AGE-BSA was then removed by washing the wells three times with PBS-Tween buffer. The cross-linked AGE-BSA to the tail tendon coated plate was then quantitated by the polyclonal antibody raised against AGE-RNase. After a one-hour incubation period, AGE antibody was removed by washing 4 times with PBS-Tween.

The bound AGE antibody was then detected with the addition of horseradish peroxidase-conjugated secondary antibody, e.g., goat anti-rabbit immunoglobulin and incubation for 30 minutes. The substrate of 0.1 M citrate buffer containing 0.03% $H_2O_2$ (2 yield #00-2008) and 2,2-azino-di(3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

% inhibition={[Optical density (without compound)−optical density (with compound)]/optical density (without compound)]} 100%

The $IC_{50}$ relative inhibition by various test compounds at 10 mM is as follows:

| Test Compound | $IC_{50}$ |
|---|---|
| 3,4-diamino-6-methyl-1,2,4-triazine-5(4H)-one; | 0.13 |
| 3,4-diamino-6-(4-hydroxybenzyl)-1,2,4-triazine-5(4H)-one hydrochloride | 1.7 |
| 3,4-diamino-6-ethyl-1,2,4-triazine-5(4H)-one hydrochloride | 1.54 |
| 3,4-diamino-6-benzyl-1,2,4-triazine-5(4H)-one hydrochloride | 11.4 |
| 3,4-diamino-6-(2'-carboxyethyl)-1,2,4-triazine-5(4H)-one | 1.6 |
| 3,4-diamino-6-(2-methypropyl)-1,2,4-triazine-5(4H)-one | 5.1 |
| 3,4-diamino-6-(1'-ethoxycarbonylethyl-1,2,4-triazine-5(4H)-one hydrochloride | 1.85 |
| 3,4-diamino-6-(1'-ethoxycarbonylheptyl-1,2,4-triazine-5(4H)-one hydrochloride | 6.6 |
| 6-(3',4'-diamino-5(4H)-one-1,2,4-triazinyl)hydrazide | 0.73 |
| 3-[6'-(3',4'-diamino-5'(4H)-one-1',2',4'-triazinyl)]-propionic hydrazide hydrochloride | 0.5 |
| 2-methyl-6'-(3',4'-diamino-5(4H)-one-1,2,4-triazinyl)hydrazide | 3.5 |
| 4-amino-3-hydrazino-6-methyl-1,2,4-triazine-5(4H)-one hydrochloride | 0.016 |
| 4-amino-3-hydrazino-6-(4-hydroxybenzyl)-1,2,4-triazine-5(4H)-one hydrochloride | 0.45 |
| 4-amino-3-hydrazino-1,2,4-triazine-5(4H)-one hydrochloride | 1.56 |

The above experiment suggests that this type of drug therapy has benefits in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints.

EXAMPLE 6

The following method was used to evaluate the ability of the compounds of the present invention to inhibit the cross-linking of N-acetyl glycyl-lysine methyl ester in the presence of ribose.

Materials:
N-acetylglycyllysine methyl ester (DP in formula below)
Ribose (R in formula below)
Test compounds (C in formula below)

Reagents:
0.5 M sodium phosphate buffer pH 7.4
N-acetylglycyllysine methyl ester in 0.5M sodium phosphate buffer, pH 7.4
Ribose: 800 mM
Test compounds dissolved in the above buffer and the pH is adjusted to 7.4, if necessary Procedure:
Reaction mixtures are prepared as follows:

| | | | |
|---|---|---|---|
| 80 mg/ml N-acetylglycyllysine methyl ester/buffer | 0.1 | 0.1 | — |
| ribose | 0.1 | 0.1 | 0.1 |
| test compound | — | 0.1 | 0.1 |
| buffer | 0.2 | 0.1 | 0.2 | and incubated at 37° C. for 16–24 hours. At the end of the incubation period reaction mixture is diluted with 3 ml distilled water and the fluorescence is read using an excitation wavelength of 350 nm and emission wavelength of 100 nm. The inhibition of the cross-linking is calculated from the decrease in the fluorescence in the presence of the test compounds according to the formula:

Inhibition (%)=100×[DPRC fluorescence−RC fluorescence]/DPR fluorescence

The Inhibition by various test compounds ($IC_{50}$) is as follows:

| Test compound | $IC_{50}$ mM |
|---|---|
| 3,4-diamino-6-methyl-1,2,4-triazine-5(4H)-one; | 1.23 |
| 3,4-diamino-6-(4-hydroxybenzyl)-1,2,4-triazine-5(4H)-one hydrochloride | 4.4 |
| 3,4-diamino-6-ethyl-1,2,4-triazine-5(4H)-one hydrochloride | 2 |
| 3,4-diamino-6-benzyl-1,2,4-triazine-5(4H)-one hydrochloride | 1.2 |
| 3,4-diamino-6-(3,4-dimethoxystyryl)-1,2,4-triazine-5(4H)-one hydrochloride | 0.35 |
| 3,4-diamino-6-(2'-nitrobenzyl)-1,2,4-triazine-5(4H)-one hydrochloride | 0.9 |
| 3,4-diamino-6-(2'-carboxyethyl)-1,2,4-triazine-5(4H)-one | 1.97 |
| 3,4-diamino-6-isopropyl-1,2,4-triazine-5(4H)-one hydrochloride | 1.05 |
| 3,4-diamino-6-(2-methypropyl)-1,2,4-triazine-5(4H)-one | 1.16 |
| 3,4-diamino-6-propyl-1,2,4-triazine-5(4H)-one hydrochloride | 1.3 |
| 3,4-diamino-6-butyl-1,2,4-triazine-5(4H)-one | 1.6 |
| 3,4-diamino-6-(1-methylpropyl)-1,2,4-triazine-5(4H)-one | 1.4 |
| 3,4-diamino-6-cyclopropyl-1,2,4-triazine-5(4H)-one | 2 |
| 3,4-diamino-6-phenethyl-1,2,4-triazine-5(4H)-one hydrochloride | 2.7 |
| 3,4-diamino-6-carboxyethyl-1,2,4-triazine-5(4H)-one hydrochloride | 0.72 |
| 3,4-diamino-6-(2'-ethoxycarbonylethyl-1,2,4-triazine-5(4H)-one hydrochloride | 0.84 |
| 3,4-diamino-6-(1'-ethoxycarbonylethyl-1,2,4-triazine-5(4H)-one hydrochloride | 1.65 |
| 3,4-diamino-6-(1'-ethoxylcarbonylheptyl-1,2,4-triazine-5(4H)-one hydrochloride | 0.48 |
| 3,4-diamino-6-(3'-methoxyphenylcarbonyl-methylene)-1,2,4-triazine-5(4H)-one hydrochloride | >10 |
| 6-(3',4'-diamino-5(4H)-one-1,2,4-triazinyl)hydrazide | 0.73 |
| 3-[6'-(3',4'-diamino-5'(4H)-one-1',2',4'-triazinyl)]-propionic hydrazide hydrochloride | 1.5 |

| Test compound | IC$_{50}$mM |
|---|---|
| 2-methyl-6'-(3',4'-diamino-5(4H)-one-1,2,4-triazinyl)hydrazide | 0.83 |
| 3,4-diamino-6-(1',1'-dimethyl-2'-hydroxyethyl)-1,2,4-triazine-5(4H)-one | 0.97 |
| 4-amino-3-hydrazino-6-methyl-1,2,4-triazine-5(4H)-one hydrochloride | <3 |
| 4-amino-3-hydrazino-6-(4-hydroxybenzyl)-1,2,4-triazine-5(4H)-one hydrochloride | >1 |
| 4-amino-3-hydrazino-1,2,4-triazine-5(4H)-one hydrochloride | >10 |

The above experiment suggests that this type of drug therapy will reduce the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly damage to tendons, ligaments and other joints.

EXAMPLE 7

| Tablet | mg/tablet |
|---|---|
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a 11/32" punch with a hardness of 4 kg. These tablets will disintegrate within a half hour according to the method described in USP XVI.

EXAMPLE 8

| Lotion | mg/g |
|---|---|
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 9

| Oral Rinse | |
|---|---|
| Compound of Formula I: | 1.4% |
| Chlorhexidine gluconate | 0.12% |

| Oral Rinse | |
|---|---|
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 10

| Toothpaste | |
|---|---|
| Compound of Formula I: | 5.5% |
| Sorbitol, 70% in water | 25% |
| Sodium saccharin | 0.15% |
| Sodium lauryl sulfate | 1.75% |
| Carbopol 934, 6% dispersion in | 15% |
| Oil of Spearmint | 1.0% |
| Sodium hydroxide, 50% in water | 0.76% |
| Dibasic calcium phosphate dihydrate | 45% |
| Water to | 00% |

EXAMPLE 11

To further study the ability of inhibitors of nonenzymatic browning to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 mM glucose-6-phosphate in a 0.5 M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed. Incubation of the disks in glucose-6-phosphate alone shows slight brown color versus disks soaked in buffer alone. Inclusion of chlorhexidine (in the form of Peridex® at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A pharmaceutical composition comprising an amount a compound of the formula:

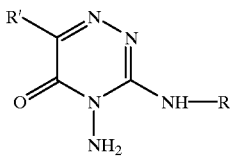

wherein the amount is effective for (i) improving the elasticity or reducing wrinkles of the skin, treating (ii) diabetes, or treating or ameliorating (iii) hypertension, (iv) adverse sequelae of diabetes, (v) kidney damage, (vi) damage to blood vasculature, (vii) retinopathy, (viii) damage to lens proteins, (ix) cataracts, (x) peripheral neuropathy, (xi) osteoarthritis, or (xii) damage to a tissue caused by contact with elevated levels of reducing sugars,
wherein R is hydrogen or an amino group;
R' is:
  a (C3 to C7)cycloalkyl group;
  a (C6 or C10)aryl(C1 to C7)alkyl group or (C6 or C10)arylethenyl group wherein the alkyl portion has from 1 to 6 carbon atoms, and the aryl portion is optionally substituted by one to three hydroxy, alkoxy or nitro groups, wherein where R is $NH_2$, R' is not phenymethyl substituted with only alkoxy;
  a heteroaryl group having from 5 to 6 ring atoms including one to three heteroatoms selected from oxygen, nitrogen or sulfur;
  a group of the formula —C(O)—R" wherein R" is a hydroxy, a (C1 to C7)alkoxy group, a (C6 or C10) aryl group optionally substituted by a (C1 to C7)alkoxy group, or a group of the formula —NR'"—NH2, wherein R'" is hydrogen or a methyl group; or
  a (C1 to C7)alkyl group or (C2 to C6)alkenyl group substituted by hydroxy or a group of the formula —C(O)—$R^{2'}$, $R^{2'}$ is a hydroxy, a (C1 to C7)alkoxy group, (C6 or C10)aryl group optionally substituted by a (C1 to C7)alkoxy group, or a group of the formula —NR""—$NH_2$ wherein R"" is hydrogen or a methyl group;
and their pharmaceutically acceptable acid addition salts.

2. The composition of claim 1, wherein the compound comprises 3-(6'-(3'4'-diamino-5'(4H)-one-1',2',4'-triazinyl))-propionic hydrazide hydrochloride, or another pharmaceutically acceptable salt thereof.

3. The composition of claim 1, wherein the compound comprises 4-amino-3-hydrazino-6-(4-hydroxybenzyl)-1,2,4-triazin-5(4H)-one hydrochloride, or another pharmaceutically acceptable salt thereof.

4. A method for, in an animal, (i) improving the elasticity or reducing wrinkles of the skin, treating (ii) diabetes, or treating or ameliorating (iii) hypertension, (iv) adverse sequelae of diabetes, (v) kidney damage, (vi) damage to blood vasculature, (vii) retinopathy, (viii) damage to lens proteins, (ix) cataracts, (x) peripheral neuropathy, (xi) osteoarthritis, or (xii) damage to a tissue caused by contact with elevated levels of reducing sugars, the method comprising administering to the animal an effective amount of a compound of the formula:

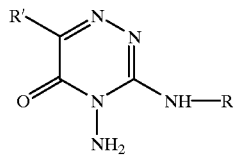

wherein R is hydrogen or an amino group;
R' is:
  a (C3 to C7)cycloalkyl group;
  a (C6 or C10)aryl(C1 to C7)alkyl group or (C6 or C10)arylethenyl group wherein the alkyl portion has from 1 to 6 carbon atoms, and the aryl portion is optionally substituted by one to three hydroxy, alkoxy or nitro groups;
  a heteroaryl group having from 5 to 6 ring atoms including one to three heteroatoms selected from oxygen, nitrogen or sulfur;
  a group of the formula —C(O)—R" wherein R" is a hydroxy, a (C1 to C7)alkoxy group, a (C6 or C10) aryl group optionally substituted by a (C1 to C7)alkoxy group, or a group of the formula —NR'"—NH2, wherein R'" is hydrogen or a methyl group; or
  a (C1 to C7)alkyl group or (C2 to C6)alkenyl group substituted by hydroxy or a group of the formula —C(O)—$R^{2'}$, $R^{2'}$ is a hydroxy, a (C1 to C7)alkoxy group, (C6 or C10)aryl group optionally substituted by a (C1 to C7)alkoxy group, or a group of the formula —NR""—$NH_2$ wherein R"" is hydrogen or a methyl group;
and their biologically or pharmaceutically acceptable acid addition salts, together with a carrier therefor.

5. A method according to claim 4, wherein the administered compound comprises 3,4-diamino-6-(2'-ethoxycarbonylethyl)-1,2,4-triazin-5(4H)-one, or a pharmaceutically acceptable salt thereof.

6. A method according to claim 4, wherein the administered compound comprises 3,4-diamino-6-(1'-ethoxycarbonylheptyl)-, 1,2,4-triazin-5(4H)-one, or a pharmaceutically acceptable salt thereof.

7. The method of claim 4, wherein R is hydrogen.

8. The method of claim 7, wherein the administered compound comprises 3,4-diamino-6-methyl-1,2,4-triazin-5(4H)-one, or a pharmaceutically acceptable salt thereof.

9. The method of claim 7, wherein the administered compound comprises 3,4-diamino-6-ethyl-1,2,4-triazin-5(4H)-one hydrochloride, or another pharmaceutically acceptable salt thereof.

10. The method of claim 7, wherein the administered compound comprises 3-(6'-(3',4'-diamino-5'(4H)-one-1',2',4'-triazinyl))-propionic hydrazide hydrochloride, or another pharmaceutically acceptable salt thereof.

11. The method of claim 7, wherein the administered compound comprises 3,4-diamino-6-(4-hydroxybenzyl)-1,2,4-triazin-5(4H)-one hydrochloride or another pharmaceutically acceptable salt thereof.

12. The method of claim 7, wherein R is an amino group.

13. The method of claim 12, wherein the administered compound comprises 4-amino-3-hydrazino-6-methyl-1,2,4-triazin-5(4H)-one hydrochloride, or another pharmaceutically acceptable salt thereof.

14. The method of claim 12, wherein the administered compound comprises 4-amino-3-hydrazino-6-(4- hydroxybenzyl)-1,2,4-triazin-5(4H)-one hydrochloride, or another pharmaceutically acceptable salt thereof.

15. A method according to claim 12, wherein the administered compound comprises 3,4-diamino-6-(4-hydroxybenzyl)-1,2,4-triazin-5(4H)-one hydrochloride, or another pharmaceutically acceptable salt thereof.

* * * * *